(12) United States Patent
Kalentun et al.

(10) Patent No.: US 12,257,130 B2
(45) Date of Patent: Mar. 25, 2025

(54) INCONTINENCE PAD WITH VARYING THICKNESS PROFILE

(71) Applicant: Essity Hygiene and Health Aktiebolag, Gothenburg (SE)

(72) Inventors: Pia Kalentun, Gothenburg (SE); Marie Kristensson, Gothenburg (SE)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 982 days.

(21) Appl. No.: 17/294,791

(22) PCT Filed: Dec. 7, 2018

(86) PCT No.: PCT/EP2018/084022
§ 371 (c)(1),
(2) Date: May 18, 2021

(87) PCT Pub. No.: WO2020/114612
PCT Pub. Date: Jun. 11, 2020

(65) Prior Publication Data
US 2021/0401632 A1 Dec. 30, 2021

(51) Int. Cl.
*A61F 13/15* (2006.01)
*A61F 13/47* (2006.01)
(Continued)

(52) U.S. Cl.
CPC .... *A61F 13/15203* (2013.01); *A61F 13/4704* (2013.01); *A61F 13/4758* (2013.01);
(Continued)

(58) Field of Classification Search
CPC ........ A61F 13/15; A61F 13/47; A61F 13/475; A61F 13/537; A61F 13/551;
(Continued)

(56) References Cited

U.S. PATENT DOCUMENTS 5,934,470 A 8/1999 Bauer et al.
6,063,065 A 5/2000 Costa
(Continued)

FOREIGN PATENT DOCUMENTS

CA 2019455 A1 11/1991
CN 1652736 A 8/2005
(Continued)

OTHER PUBLICATIONS

Office Action (Decision of Rejection) issued Jan. 5, 2023, by the National Intellectual Property Administration, P. R. China in Chinese Patent Application No. 201880098929.9 and an English translation of the Office Action. (18 pages).
(Continued)

*Primary Examiner* — Michele Kidwell
(74) *Attorney, Agent, or Firm* — Buchanan Ingersoll & Rooney, PC

(57) ABSTRACT

The incontinence pad comprises a fluid permeable topsheet, a backsheet and an absorbent core being located between the topsheet and the backsheet. The absorbent core comprises a first core layer and a fluid control layer. The first core layer comprises 100 gsm superabsorbent material or more. The absorbent core has a varying thickness profile as seen in the longitudinal direction (L), with a first thickness (T1) in the intermediate portion and a second thickness (T2) in the rear portion. The first thickness (T1) in the intermediate portion is from 9 mm or more and the second thickness (T2) is 4 mm or less, as measured under a load of load of 0.5 kPa. The region which has the second thickness (T2) extends 30 mm or more in the longitudinal direction (L) from the core rear edge and toward the core front edge.

20 Claims, 4 Drawing Sheets

(51) Int. Cl.
*A61F 13/475* (2006.01)
*A61F 13/53* (2006.01)
*A61F 13/537* (2006.01)
*A61F 13/551* (2006.01)

(52) U.S. Cl.
CPC .......... *A61F 13/537* (2013.01); *A61F 13/551* (2013.01); *A61F 2013/15146* (2013.01); *A61F 2013/15373* (2013.01); *A61F 2013/530481* (2013.01)

(58) Field of Classification Search
CPC ................. A61F 13/534; A61F 13/535; A61F 2013/5355; A61F 13/47227; A61F 13/47218; A61F 13/1702; A61F 2013/15373; A61F 2013/15365
See application file for complete search history.

(56) References Cited

U.S. PATENT DOCUMENTS

| | | | |
|---|---|---|---|
| 6,437,214 B1 * | 8/2002 | Everett | A61F 13/5376 604/378 |
| 7,122,713 B2 | 10/2006 | Komatsu et al. | |
| 7,959,622 B2 | 6/2011 | Kudo et al. | |
| 8,444,617 B2 * | 5/2013 | Wennerback | A61F 13/496 604/385.01 |
| 11,045,362 B2 * | 6/2021 | Guidotti | A61F 13/535 |
| 2006/0178650 A1 * | 8/2006 | Hakansson | A61F 13/53713 604/378 |
| 2008/0275419 A1 | 11/2008 | Standfest | |
| 2011/0073513 A1 | 3/2011 | Weisman et al. | |
| 2011/0139662 A1 | 6/2011 | Hird et al. | |
| 2012/0316533 A1 | 12/2012 | Norimoto | |
| 2013/0131623 A1 | 5/2013 | Kawakami | |
| 2013/0144241 A1 * | 6/2013 | Persson | A61F 13/53713 604/378 |
| 2016/0015577 A1 | 1/2016 | Vartiainen et al. | |
| 2016/0136012 A1 * | 5/2016 | Peri | A61F 13/53752 604/374 |
| 2016/0310330 A1 * | 10/2016 | Knos | A61F 13/15723 |
| 2018/0303681 A1 * | 10/2018 | Back | A61F 13/534 |
| 2018/0344539 A1 | 12/2018 | Kurihara et al. | |
| 2020/0306099 A1 | 10/2020 | Viens et al. | |
| 2021/0401631 A1 | 12/2021 | Kalentun et al. | |

FOREIGN PATENT DOCUMENTS

| | | | | |
|---|---|---|---|---|
| CN | 1684883 | A | 10/2005 | |
| CN | 101541279 | A | 9/2009 | |
| CN | 101810530 | A | 8/2010 | |
| CN | 201591694 | U | 9/2010 | |
| CN | 102573726 | A | 7/2012 | |
| CN | 102887293 | A | 1/2013 | |
| CN | 102958481 | A | 3/2013 | |
| CN | 103096852 | A | 5/2013 | |
| CN | 104379105 | A | 2/2015 | |
| CN | 105143051 | A | 12/2015 | |
| CN | 112912043 | A | 6/2021 | |
| EP | 0 397 110 | * | 11/1990 | ............. A61F 13/46 |
| EP | 2589356 | A1 | 5/2013 | |
| EP | 3384887 | A1 | 10/2018 | |
| GB | 2304586 | A | 3/1997 | |
| JP | H08-508455 | A | 9/1996 | |
| JP | 2006230596 | A | 9/2006 | |
| JP | 2009148441 | A | 7/2009 | |
| JP | 2012187354 | A | 10/2012 | |
| JP | 2015500055 | A | 1/2015 | |
| JP | 2015519154 | A | 7/2015 | |
| JP | 2016509954 | A | 4/2016 | |
| JP | 2017515571 | A | 6/2017 | |
| JP | 2018050714 | A | 4/2018 | |
| WO | 2008069138 | A1 | 6/2008 | |
| WO | 2013081515 | A1 | 6/2013 | |
| WO | 2013185800 | A1 | 12/2013 | |
| WO | 2014142720 | A1 | 9/2014 | |
| WO | 2015174896 | A1 | 11/2015 | |
| WO | 2018117932 | A1 | 6/2018 | |

OTHER PUBLICATIONS

Office Action issued in U.S. Appl. No. 17/294,771, dated Aug. 7, 2024, 27 pages.
Office Action (Notification of the Second Office Action) issued on Jul. 14, 2022, by the Chinese Patent Office in corresponding Chinese Patent Application No. 201880098924.6, and an English Translation of the Office Action. (20 pages).
Notification of the Second Office Action issued on May 11, 2022, by the Chinese Patent Office in corresponding Chinese Patent Application No. 201880098929.9, and an English Translation of the Office Action. (25 pages).
Office Action issued in U.S. Appl. No. 17/294,771, dated Feb. 1, 2024, 24 pages.
Notification of the First Office Action issued on Oct. 29, 2021, by the Chinese Patent Office in corresponding Chinese Patent Application No. 201880098929.9, and an English Translation of the Office Action. (23 pages).
International Search Report (PCT/ISA/210) and Written Opinion (PCT/ISA/237) mailed on Aug. 14, 2019, by the European Patent Office as the International Searching Authority for International Application No. PCT/EP2018/084022.
International Search Report (PCT/ISA/210) and Written Opinion (PCT/ISA/237) mailed on Jun. 24, 2019, by the European Patent Office as the International Searching Authority for International Application No. PCT/EP2018/084016.
Office Action (Communication) issued on Apr. 12, 2023, by the European Patent Office in corresponding European Patent Application No. 18 822 291.3. (5 pages).
Office Action issued on Mar. 27, 2023, by the Colombian Patent Office in corresponding Colombian Patent Application No. NC2021/0007253, and an English Translation of the Office Action. (18 pages).
Examination report issued in corresponding Australian Patent Application No. 2018452056, dated Sep. 21, 2021 (5 pages).
First Office Action issued in corresponding Chinese Patent Application No. 201880098924.6, dated Nov. 25, 2021, with English Translation (22 pages).
Office Action (Communication) issued on Sep. 29, 2022, by the European Patent Office in corresponding European Patent Application No. 18 822 291.3. (4 pages).
Office Action (Notice of Reasons for Rejection) issued on Aug. 8, 2022, by the Japanese Patent Office in corresponding Japanese Patent Application No. 2021-532053, and an English Translation of the Office Action. (15 pages).
Office Action (Notice of Reasons for Rejection) issued on Aug. 29, 2022, by the Japanese Patent Office in corresponding Japanese Patent Application No. 2021-532057, and an English Translation of the Office Action. (6 pages).
Search Report and Written Opinion issued on Sep. 7, 2022, by the Brazilian Patent Office in corresponding Brazilian Application No. BR112021007981-5. (4 pages).
Search Report and Written Opinion issued on Sep. 7, 2022, by the Brazilian Patent Office in corresponding Brazilian Application No. BR112021007977-7. (4 pages).
Office Action (Communication pursuant to Article 94(3) EPC) issued on Oct. 25, 2023, in European Patent Application No. 18822291.3. (3 pages).
Office Action (Decision of Rejection) issued on Apr. 10, 2023, in Japanese Patent Application No. 2021-532057 and English translation of the Office Action. (6 pages).
Office Action issued on Aug. 30, 2023, in Japanese Patent Application No. 2021-532057 and English translation of the Office Action. (4 pages).
Office Action (Decision of Rejection) issued on Mar. 13, 2023, by the Japanese Patent Office in corresponding Japanese Patent Appli-

(56) References Cited

OTHER PUBLICATIONS cation No. 2021-532053, and an English Translation of the Office Action. (9 pages).

* cited by examiner

INCONTINENCE PAD WITH VARYING THICKNESS PROFILE

TECHNICAL FIELD

The present invention relates to a profiled urine incontinence pad. The present invention also relates to an individually wrapped urine incontinence pad and a stack of folded profiled urine incontinence pads.

BACKGROUND OF THE INVENTION

Urine incontinence pads are well known articles of commerce. Such articles may be absorbent pads for heavier bladder leakage or thinner liners for light bladder leakage.

Incontinence pads are generally provided with an absorbent core to receive and retain body liquids. For incontinence pads intended for heavier bladder leakage to function efficiently, the absorbent core must quickly acquire body liquids into the structure from the point of application and subsequently distribute the body liquids within and throughout the absorbent core to provide maximum leakage containment. It is also desirable that such pads are comfortable and have a good fit, i.e. to be sized and configured to fit the limited space available in the crotch portion of the underwear while providing the wearer with a feeling of security. Additionally, there is desire that such articles are discreet, thin and not visible even if the user wears tighter clothes, which may be seen as being in contradiction with the above objects.

When an incontinence pad is used by a wearer, it is exposed to pressure, which tends to compress the article in a thickness direction. Such pressures are typically about 2-5 kPa when standing or walking, about 10-20 kPa when sitting, 30 kPa when sitting and leaning forward, and up to 50 kPa when bicycling, in the centre of an absorbent pad. In order to maintain excellent liquid distribution properties in the absorbent article, it is important that the absorbent core can withstand pressures and not collapse when exposed to higher pressures.

A further desire is that the pads should be neat and easily foldable to obtain individual package sizes for easy bring along of the article in a bag or pocket and for easy disposal after use.

It is therefore an object of the present invention to provide an improved urine incontinence pad which may receive larger urine insults, is comfortable and gives the user a sense of high security throughout the daily activities, while still being discreet and thin. There is also an aim to improve the folding and packaging solution for such incontinence pads.

SUMMARY OF THE INVENTION

One or more of the above objects may be achieved with a urine incontinence pad in accordance with claim 1, an individually wrapped urine incontinence pad according to claim 19 and a stack of folded incontinence pads according to claim 20. Further embodiments are set out in the dependent claims, in the following description and in the drawings.

The urine incontinence pad as disclosed herein and according to a first aspect has longitudinal side edges and transverse end edges. The urine incontinence pad further comprises a fluid permeable topsheet, a backsheet and an absorbent core being located between the topsheet and the backsheet. The absorbent core has a core front edge, a core rear edge, a core first longitudinal side edge and a core second longitudinal side edge. The absorbent core comprises a first core layer and a fluid control layer. The absorbent core has in its longitudinal direction a front portion, a rear portion and an intermediate portion located between the front portion and the rear portion. The front portion and the rear portion each have a length of about 30% of the total length of the absorbent core. The intermediate portion has a length of about 40% of the total length of the absorbent core and the first core layer extends over the front portion, the intermediate portion and the rear portion. The fluid control layer is shorter than the first core layer and extends in the front portion and the intermediate portion. The first core layer comprises 100 gsm superabsorbent material or more. The absorbent core has a varying thickness profile as seen in the longitudinal direction, with a first thickness in the intermediate portion and a second thickness in the rear portion, the first thickness in the intermediate portion being from 9 mm or more and the second thickness being 4 mm or less, as measured under a load of 0.5 kPa. The region having the second thickness extends 30 mm or more from the core rear end edge and toward the core front end edge.

The portion of the core comprising the fluid control layer may have the first thickness T1 and the portions of the core outside the fluid control layer may have the second thickness T2.

The region having the second thickness may extend from the first longitudinal side of the absorbent core to the second longitudinal side of the absorbent core.

The superabsorbent material may for example be substantially homogenously mixed in the first core layer or be provided as a sub-layer in the first core layer.

The urine incontinence pad according to the present disclosure has a relatively thick intermediate portion giving the wearer a sense of comfort and leakage security. The fit will also be improved as the pad conforms well to the wearer's anatomy. The pad comes into close body contact with the wearer in the crotch region due to the thicker intermediate portion, thereby allowing excreted liquid to be directly absorbed into the absorbent core and reducing the risk of side leakage. However, the solution according to the present disclosure also provides a highly discreet urine incontinence pad as the rear portion of the absorbent core has a thickness of less than 4 mm in a portion extending 30 mm or more from the core rear end edge and towards the core front end edge. A varying thickness profile with a considerably greater thickness in the intermediate portion than in the rear portion has been found by the present inventors to improve the leakage security and the perception by the wearer of comfort and good leakage perception while at the same time giving a highly discreet urine incontinence pad which is almost invisible when worn by the wearer as the rear portion is so thin in an area extending 30 mm or more from the core rear end edge.

The second thickness may be 4 mm or less, such as from 3.5 to 0.3 mm or from 3.0 mm to 1.0 mm.

The first thickness may be from 9 mm or more, such as from 9 mm to 16 mm, or 9 mm to 12 mm.

The varying thickness profile as seen in the longitudinal direction of the absorbent core may have a third thickness in the rear portion or in a transitional region comprising a part of the intermediate portion and a part of the rear portion, the third thickness may be from 4.5 mm to 8.5 mm. Such third thickness, being an intermediate thickness compared to the first and the second thickness, may increase the comfort of the incontinence pad by providing a softer transition between the first and the second thickness regions.

The third thickness may also facilitate the folding of the articles when provided in a stack, if the folding line is in this region of the core instead of the thickest region.

The absorbent core may have the first thickness in from 15 to 40% of the total longitudinal length of the absorbent core in the front portion, in a portion extending from the intermediate portion and towards the core front edge.

Hence, the portion of the absorbent core having the first thickness may be relatively large, with a portion in the front region and a portion in the rear region being very thin. Such configuration will lead to a feeling of high leakage security while at the same time offering a very discreet incontinence pad.

The intermediate portion may have a first thickness under a load of 0.5 kPa and a second thickness under a load of 2.5 kPa, and wherein a difference between the first thickness and the first compressed thickness may be less than 25%, such as 20% or less. Such compression resistant absorbent core provides an efficient fluid absorbency that will maintain its structure and fluid flow control properties when pressure is exerted on the absorbent core during use of the urine incontinence pad.

The absorbent core may comprise from 200 gsm to 1000 gsm superabsorbent material at least in the part of the absorbent core having the first thickness and/or in part of the absorbent core having the third thickness, providing the intermediate portion with a high absorbency in region of the pad arranged in the crotch region of the wearer.

The superabsorbent material may be homogenously mixed within the layers making up the absorbent core, but it may be unevenly distributed between the different layers. The superabsorbent material may also for example be provided as sub-layers within the layers making up the absorbent core.

The first core layer may comprise between 100 and 200 gsm superabsorbent material at least in the part of the absorbent core having the second thickness, allowing the thin layer to have a fairly high absorbency also in the rear and/or front portions.

The first core layer may have a waist portion located in the front portion or between the front portion and the intermediate portion. A width of the waist portion may be from 50 to 75% of a widest transverse width of the front portion of the first absorbent layer. The narrower waist portion located in the front portion or between the front portion and the intermediate portion may further ensure that the article has a proper fit in a wearer's groin and stays in place during use. That the incontinence pad stays in place during use ensure high leakage prevention and the discretion of the incontinence pad according to the present disclosure as forward or rear displacement of the incontinence pad could lead to that the thicker region becomes more exposed and that the discretion is compromised.

The first core layer may be arranged between the fluid control layer and the fluid permeable topsheet and thus be an upper core layer.

The absorbent core may further comprise at least one underlying core layer in the form of a fluid storage layer. The fluid storage layer(s) may be located between the fluid flow control layer and the backsheet The first core layer may have an opening extending therethrough from a body-facing side of the first absorbent layer to a garment facing side of the first absorbent layer, the opening being arranged in the front portion and the intermediate portion. The opening in the first core layer may extend completely through the layer, thereby forming a cavity in the article. The opening may be arranged such that 80-100% or 90-100% of the longitudinal extension of the opening is located in the front and the intermediate portion of the first core layer in order to ensure a proper placement of the opening in relation to the wetting point of the article. About to 20% of the longitudinal extension of the opening may be located in the front portion of the first core layer. The longitudinal extension of the opening in the first core layer may be 20-40% of the longitudinal extension of the first core layer in order to ensure fluid flow into the opening and not on the outside of the topsheet. The transverse dimension of the opening may be larger in the front portion of the first core layer than the transverse dimension of the opening in the intermediate portion of the first core layer in order to improve the fluid intake rate through the opening and further into the fluid flow control structure. Thereby an absorbent article is achieved which ensures that liquid will be directed to the opening and pass into the fluid flow control structure and the core. The first core layer may have one opening only for both leakage security and improved feeling of safety for the user.

A widest transverse width of the rear portion of the absorbent core may be from 80-120 mm. This has been shown to improve comfort and leakage protection.

An elastic member may be arranged along each longitudinal side edge of the article, at least laterally outside of the core in the area of the transition between the front portion and the intermediate portion of the core. The elastic members may be located between the topsheet and the backsheet. The article may have an interspace which is free from absorbent material and which is located between the elastic member and the core in the area of the transition between the front portion and the intermediate portion of the core, more specifically in an area between the elastics, located at the periphery of the article, and the periphery of the first core layer. Each elastic member may have an extension at least to a lateral edge of a widest part of the front portion of the absorbent core to facilitate and promote folding of the first end portion of the article. Correspondingly, the elastic member may be arranged such that it does not extend in the longitudinal direction beyond the rear transversal edge of the rear part of the shorter underlying core layer in order to facilitate and promote folding of the first end portion of the incontinence pad. The elastic members may not extend beyond the first fold line of the article to facilitate fold about the fold line.

The incontinence pad may further include fastening means for fastening of the incontinence pad inside a supporting pant garment, such as a pair of underpants. The fastening means may be any conventional fastening means including adhesive and mechanical fasteners and may be covered by a releasable protective layer.

The fluid control layer which is shorter than the first core layer may be arranged not to extend into the rear portion of the absorbent core.

The absorbent core may further comprise at least one underlying core layer in the form of a fluid storage layer. The fluid storage layer(s) may be located between the fluid flow control layer and the backsheet.

The fluid storage layer may be shorter than the first core layer in each of the front portion and the rear portion and longer than the fluid control layer in each of the front portion and the rear portion.

The portion of the core outside the fluid control layer which comprises the first core layer and also the fluid storage layer may have the fourth thickness T4.

The fluid flow control structure may for example be a layered structure comprising a non-perforated fibrous polymeric layer and a first perforated polymeric layer, wherein the polymers in the first perforated polymeric layer are selected from polyolefins, polyesters, polyamides and blends and combinations thereof. The first perforated polymeric layer may have a basis weight of from 50 g/m2 to 150 g/m2, or a basis weight of from 60 g/m2 to 140 g/m2. The first perforated polymeric layer may be a nonwoven, a film or a film/nonwoven laminate. The first perforated polymeric layer may for example be a three-dimensionally formed layer having penetrating apertures. The non-perforated fibrous polymeric layer may be a high loft material of 50 g/m2 to 150 g/m2 or a basis weight of from 60 g/m2 to 140. The polymer for the non-perforated fibrous polymeric layer may be polyester. The fluid flow control structure may also be a three layer structure consisting of the non-perforated fibrous polymeric layer, the first perforated polymeric layer and a second perforated polymeric layer. The non-perforated fibrous polymeric layer may be sandwiched between the first perforated polymeric layer and the second perforated polymeric layer. The second perforated polymeric layer may also be a three-dimensionally formed layer having apertures extending from a first surface of the web towards a second surface of the web and forming protrusions on the second surface.

The fluid flow control structure may have relatively high bending stiffness. A high bending stiffness provides the absorbent article with an improved ability of resisting transverse compression between the thighs of a wearer of the article and counteracts unwanted deformation of the article during wear. The bending stiffness or flexure resistance of the laminate material in the fluid flow control structure may be 0.5-5 N, preferably 1-4 N, as measured by the modified ASTM D 4032-82 CIRCULAR BEND PROCEDURE.

Disclosed herein and according to a second aspect is an individually wrapped urine incontinence pad, comprising a urine incontinence pad and a wrapping sheet. The urine incontinence pad is a urine incontinence pad according to the first aspect. The incontinence pad has a length extending in the longitudinal direction and a width extending in a transverse direction. The wrapping sheet has a length extending in said longitudinal direction (L) and a width extending in the transverse direction. The wrapping sheet is arranged to cover the backsheet of the incontinence pad of from 75 to 95% of the length of the incontinence pad such that a first end portion, corresponding to a rear end portion of the incontinence pad, has a portion being free from the wrapping sheet. The incontinence pad is folded about a first transverse fold line with the first end portion overlying a central portion, with a second end portion being folded about a second transverse fold line and overlying the first end portion.

The incontinence pad is thus folded with an incontinence pad rear end portion first and with the front end portion overlaying the pad rear end portion such that the topsheet in the front end portion is in contact with the backsheet in the portion being free from the wrapping sheet and with the wrapping sheet covering the remaining portion of the pad rear end portion.

The wrapping sheet may also be provided with adhesive, for example, at a front edge portion for sealing against the wrapping sheet covering the incontinence pad rear end portion.

Disclosed herein and according to a third aspect is also a stack of folded incontinence pads according to the first or the second aspect. The stack comprises a plurality of urine incontinence pads wherein each of the folded incontinence pads of the plurality of folded incontinence pads is folded about a first transverse fold line with a first end portion overlying a central portion, with a second end portion being folded about a second transverse fold line and overlying the first end portion. At one of the first or the second transverse fold line, the absorbent core has the second thickness or the third thickness and at the other one of the first or second transverse fold line, the absorbent core has the first thickness. The folded incontinence pads are stacked in a head-to-toe relationship.

The first end portion may either correspond to the incontinence pad front end portion or to the incontinence pad rear end portion and the second end portion then corresponds to the other one of the front or the rear end portion.

The first end portion and the second end portion may each correspond to about 30% of the total length of the incontinence pad and the central portion may correspond to about 40% of the total length of the incontinence pad.

The fact that the absorbent core has different thicknesses at the first and the second transverse fold line may cause an unstable and uneven stack due to an uneven thickness at two of the opposing edges of the folded article. This may also lead to difficulties when packaging the folded articles in packages and non-optimal space usage within the outer packaging and unattractive packages. By stacking the folded incontinence pads in a head-to-toe relationship this problem with stacking of incontinence pads according to the present disclosure is overcome.

BRIEF DESCRIPTION OF THE DRAWINGS

The present invention will be further explained hereinafter by means of non-limiting examples and with reference to the appended drawings wherein.

DETAILED DESCRIPTION

Figure 1:
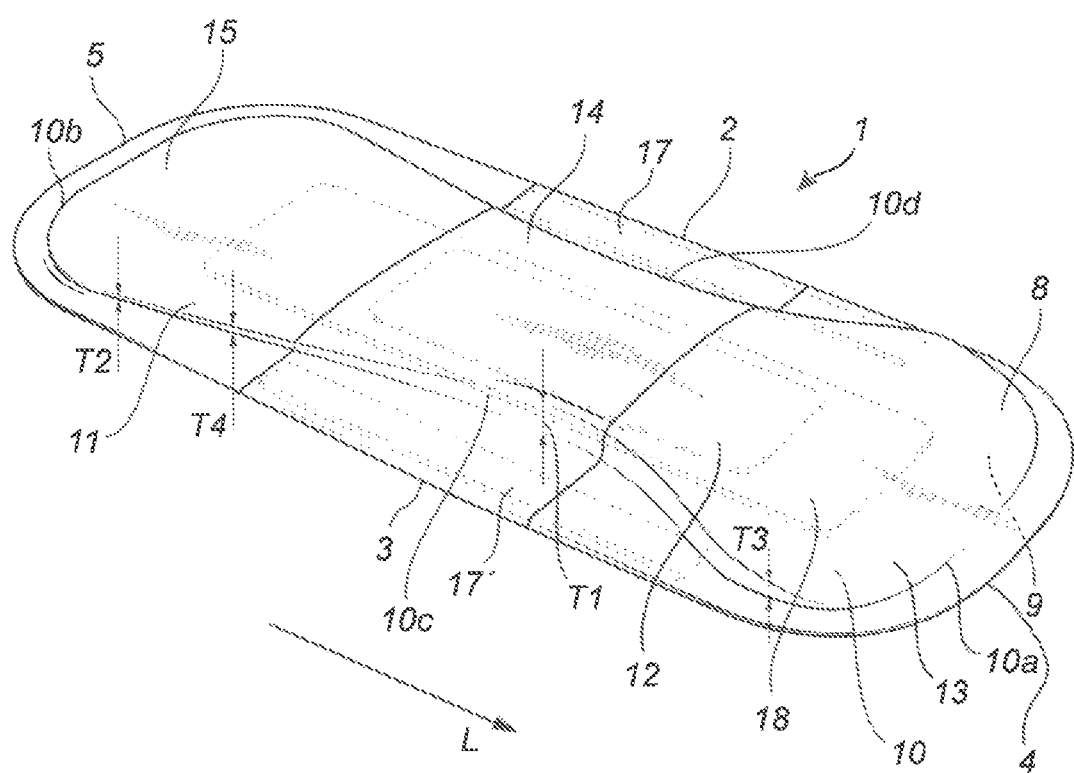
FIG. 1 shows a urine incontinence pad as disclosed herein.

The invention will be described more closely below by reference to an exemplary embodiment. The invention may however be embodied in many different forms and should not be construed as limited to the embodiments set forth in the drawings and the description thereto.

FIG. 1 schematically shows an incontinence pad 1 seen from the side that is intended to be facing towards a wearer's body when the pad 1 is being worn. The pad 1 has two longitudinal side edges 2, 3 having equal length and extending generally in the same direction. Front and rear end edges 4, 5 extend transversely at the ends of the pad 1. The rear end edge 5 is intended to be oriented rearwards, towards the buttocks of the wearer during use of the pad 1, and the front-end edge 4 is intended to be facing forwards towards the abdomen of the wearer. The pad 1 comprises a fluid permeable topsheet 8, a fluid impermeable backsheet 9 and an absorbent core 10 having a core front edge 10a, a core rear edge 10b, a core first longitudinal side edge 10c and a core second longitudinal side edge 10d. The absorbent core 10 comprises three core layers 11, 12 and 18. A first core layer 11 is located between the topsheet 8 and an underlying core layer in the form of a fluid flow control structure 12. The fluid flow control structure 12 is located between the first core layer 11 and an underlying core layer in the form of a fluid storage structure 18 located between the fluid flow control structure 12 and the backsheet 9. The absorbent core 10 is in its longitudinal direction divided into a front portion 13, an intermediate portion 14 and a rear portion 15. The front portion 13 and the rear portion 15 of the absorbent core 10 each have a length of about 30% of the total length of said absorbent core 10. The intermediate portion 14 has a length of about 40% of the total length of the absorbent core 10. The absorbent core 10 has a first thickness T1 in the intermediate portion 14 of from 9 mm or more, such as about 11 mm. The absorbent core furthermore has a second thickness T2 in the rear portion 15 of the absorbent core 10 that is 4 mm or less, such as about 3 mm. The absorbent core in this figure furthermore has a third thickness T3 in the front region which is 4 mm or less, such as about 3 mm and a fourth thickness T4 in a transitional region comprising a part of the intermediate portion 14 and a part of the rear portion, the fourth thickness T4 being from 4.5 mm to 8.5 mm. The thicknesses are measured under a load of 0.5 kPa.

The first core layer 11 extends over the front 13, the intermediate 14 and the rear portion 15 of the absorbent core 10. The flow control structure 12 partly extends over the front portion 13 and extends over the intermediate portion 14 of the absorbent core 10. A rear end edge of the flow control structure 12 is located at the transition between the intermediate portion 14 and the rear portion 15. The fluid storage layer 18 extends over the intermediate portion 14 and partly over the rear 15 and the front portion 13. The first core layer 11 and the fluid storage layer 18 may, for example, comprise a mixture of superabsorbent particles and pulp fibers. The fluid flow control structure may for example be a three layer structure consisting of a non-perforated fibrous polymeric layer, a first perforated polymeric layer and a second perforated polymeric layer. The non-perforated fibrous polymeric layer may be sandwiched between the first perforated polymeric layer and the second perforated polymeric layer. The first and second perforated polymeric layer may be a three-dimensionally formed layer having apertures extending from a first surface of the web towards a second surface of the web and forming protrusions on the second surface.

The topsheet 8 and the backsheet 9 extend together laterally outside the absorbent core 10 along the whole periphery of the absorbent core 10 and are connected to each other in an edge join along the periphery of the pad 1. The edge join may be formed in any suitable manner as known in the art such as by adhesive, ultrasonic bonding, thermobonding etc. The topsheet 8 and the backsheet 9 may consist of any material suitable for the purpose as disclosed herein, such as nonwoven or film material.

Elastic members 17, 17', such as bands or strings of elastic material, e.g. foam elastics, are arranged between the topsheet 8 and the backsheet 9 and along the longitudinal side edges 2, 3 of the pad 1. The article has an interspace which is free from absorbent material and which is located laterally between the elastic member 17, 17' and the absorbent core 10 in the transition between the front portion 13 and the intermediate portion 14 of the core 10. Each elastic member 17, 17' extends to a lateral edge of the widest part of the front portion 13 of the absorbent core 10.

An example of an article of the present disclosure is the incontinence pad of FIG. 1 having a core according to the present disclosure, a topsheet of 18 gsm spunbonded thermoplastic nonwoven material and a backsheet of 25 gsm laminate of a plastic film and a thermoplastic nonwoven material. The components of the article are connected to each other by means of adhesive and welding.

Figure 2:
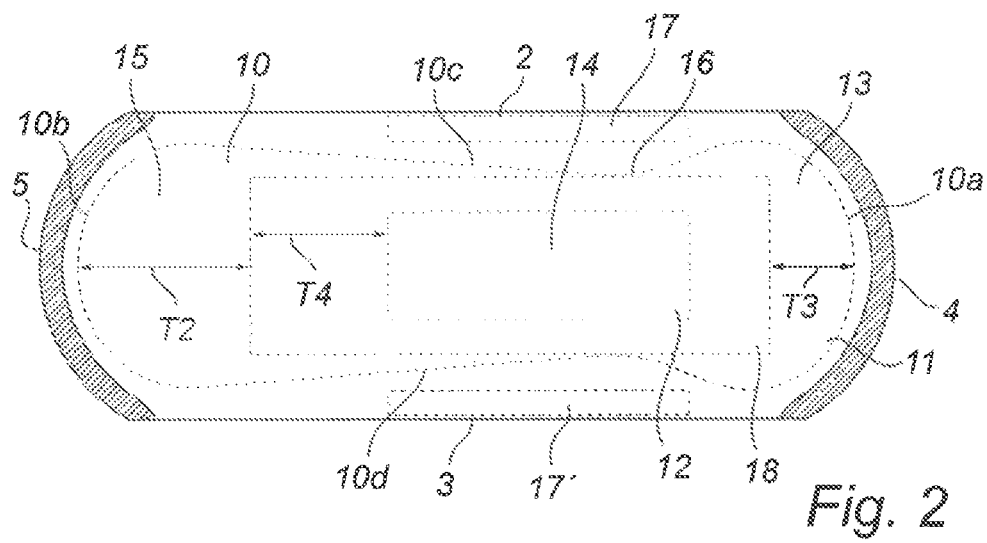
FIG. 2 shows a top plan view of a urine incontinence pad as disclosed herein.
Figure 3:
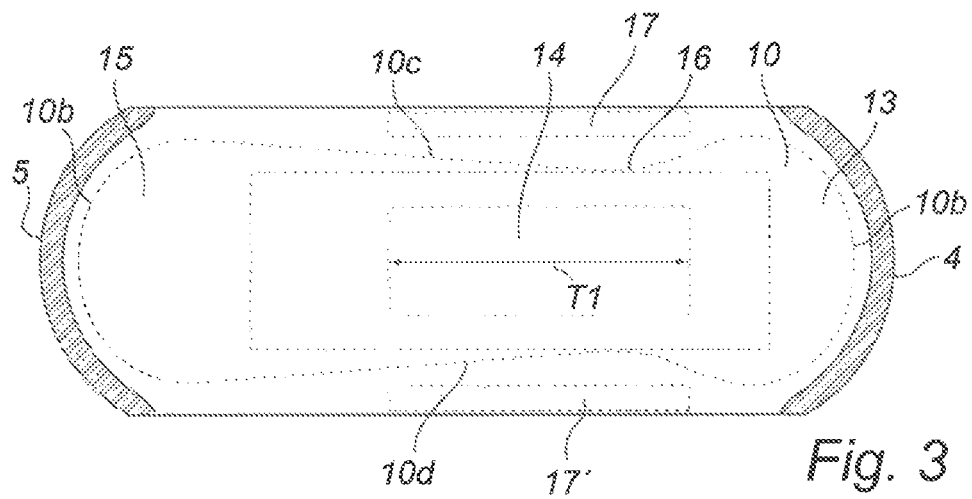
FIG. 3 shows a top plan view of a urine incontinence pad as disclosed herein.

FIGS. 2 and 3 are plan view of incontinence pads according to the present disclosure and are both seen from the side that is intended to be facing towards a wearer's body when the pad 1 is being worn. The pad 1 has two longitudinal side edges 2,3 having equal length and extending generally in the same direction. Front and rear end edges 4,5 extend transversely at the ends of the pad 1. The rear end edge is intended to be oriented rearwards during use of the pad 1, and the front-end edge 4 is intended to be facing forwards towards the abdomen of the wearer. The pad 1 comprises a fluid permeable topsheet 8, a fluid impermeable backsheet 9 and an absorbent core 10 comprising three core layers 11, 12 and 18. A first core layer 11 is located between the topsheet 8 and a fluid flow control structure 12. The fluid flow control structure 12 is located between the first core layer 11 and a fluid storage structure 18. The absorbent core 10 is in its longitudinal direction divided into a front portion 13, an intermediate portion 14 and a rear portion 15. The first core layer 11 extends over the front 13, the intermediate 14 and the rear portion 15 of the absorbent core 10. The flow control structure 12 extends over a part of the front portion 13 and over the intermediate portion 14 of the absorbent core 10. The absorbent core 10 has a narrow transversal width 16 between the front portion 13 and the intermediate portion 14 of the absorbent core 10.

Elastic members 17, 17' are arranged between the topsheet 8 and the backsheet 9 and along the longitudinal side edges 2, 3 of the pad 1. The article has an interspace free from absorbent material located laterally between the elastic members 17, 17'.

As illustrated in FIG. 2 by the arrow in the rear portion 15 marked T2, the region having the second thickness T2 extends at least 30 mm or more from the core rear edge 10b and toward the core front edge 10a, such as in a region extending from about to 40% of the total longitudinal length of the absorbent core 10. The region having the third thickness T3 extends from the core front edge 10a and towards the core rear edge 10b and is illustrated by the arrow in the front portion 13 marked T3. This region extends from about 15 mm or more from the core front edge and toward the core rear edge 10b, such as to about in from 5 to 15% of the total longitudinal length of the absorbent core 10.

The region within the arrow marked with T1 corresponds to the region of the absorbent core 10 having a thickness T1. The absorbent core has the first thickness T1 in from 15 to 40% of the total longitudinal length of the absorbent core 10 in the front portion 13, in a portion extending from the intermediate portion 14 and towards the core front edge 10a.

Figure 4A:
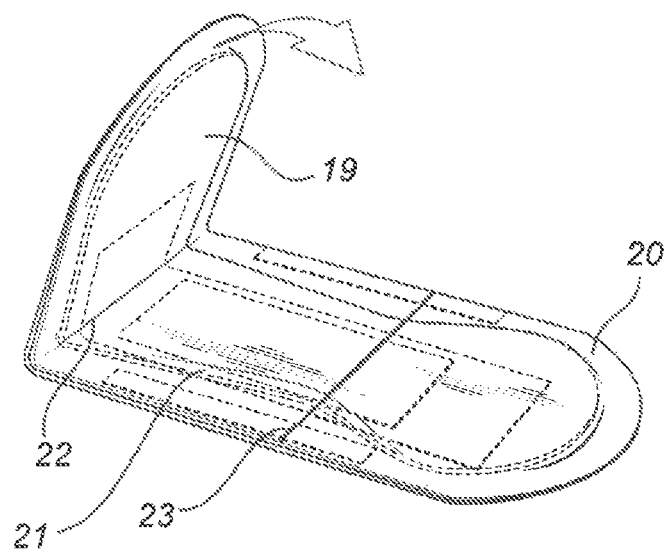
FIG. 4a-c show elevation views of successive steps of folding of a urine incontinence pad as disclosed herein.
Figure 4B:
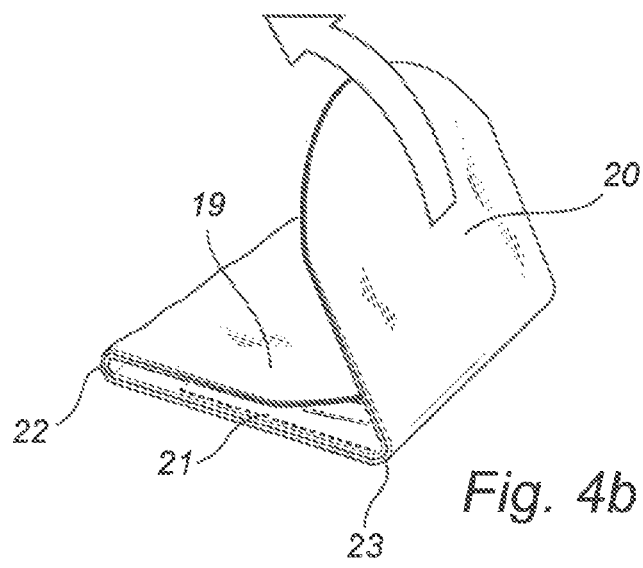
Figure 4C:
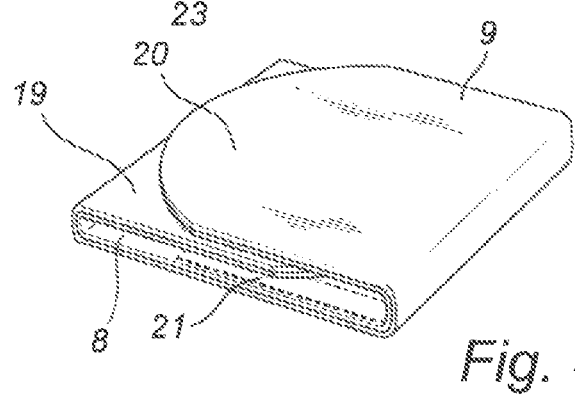

FIGS. 4a to 4c illustrate the successive folding steps of the incontinence pad 1 according to FIG. 1. In FIG. 4a a first end portion 19 of the pad 1 is folded in a first folding step about the first transversal fold line 22 coinciding with a part of the absorbent core 10 having the second thickness T2 or the fourth thickness T4 until the first end portion 19 is in contact with the central area 21 of the incontinence pad 1, i.e. folding until topsheet 8 of the first end portion 19 is in contact with the topsheet 8 of the central area 21. In this example, the first end portion 19 and the second end portion 20 correspond to about 30% of the total length of the incontinence pad 1 and the central portion 21 corresponds to about 40% of the total length of the incontinence pad 1.

FIG. 4b illustrates the second folding step, wherein a second end portion 20 of the incontinence pad 1 is folded about the second transversal fold line 23 coinciding with a part of the absorbent core 10 having the first thickness T1 of 9 mm or more, such as about 11 mm, until it is in contact with the portion 19 of the incontinence pad 1 already folded, i.e. the topsheet 8 of the second end portion 20 facing the backsheet of the first end portion 19. FIG. 4c shows the final folded incontinence pad 1. If the incontinence pad 1 is individually wrapped in a wrapping sheet, the topsheet will be facing the backsheet but also be in direct contact with the wrapping sheet.

By folding the second end portion 20 onto the first end portion 19 the second transverse folding line 23 becomes softer and less distinct and the front part of the incontinence pad 1 adopts more easily a cup-shape after unfolding and during use of the incontinence pad 1.

Figure 5:
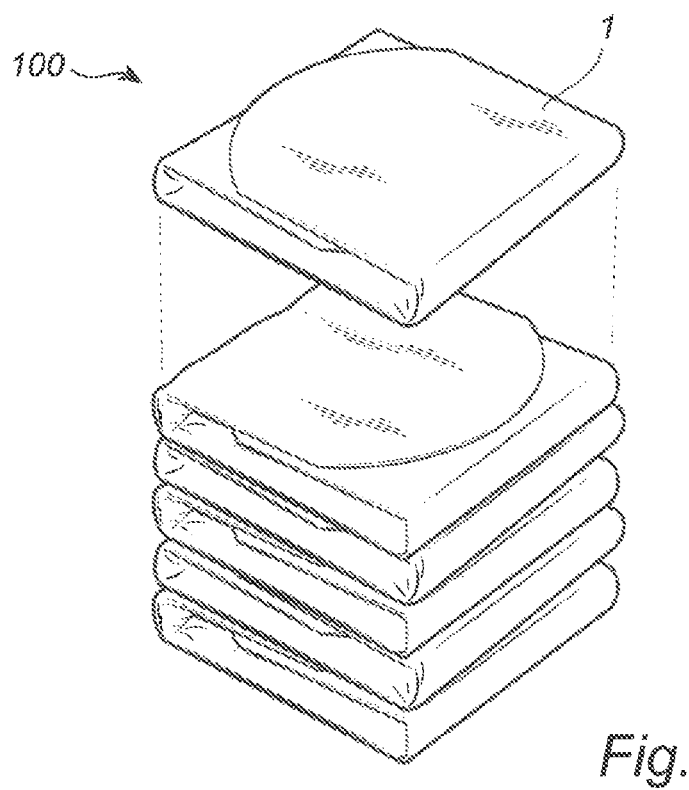
FIG. 5 is a perspective view of a stack of folded incontinence pads, comprising a plurality of urine incontinence pads as disclosed herein.

FIG. 5 illustrates a stack 100 of incontinence pads 1 according to the present disclosure. The incontinence pads 1 are stacked in a head-to-toe relationship in a head-to-toe stack 100. Due to the fact that the incontinence pad 1 has different thicknesses at the first and second transverse fold lines a head-head relationship in a stack of several such incontinence pads would lead to uneven heights at each transverse fold line and consequently unstable stacks of folded incontinence pads 100.

Figure 6:
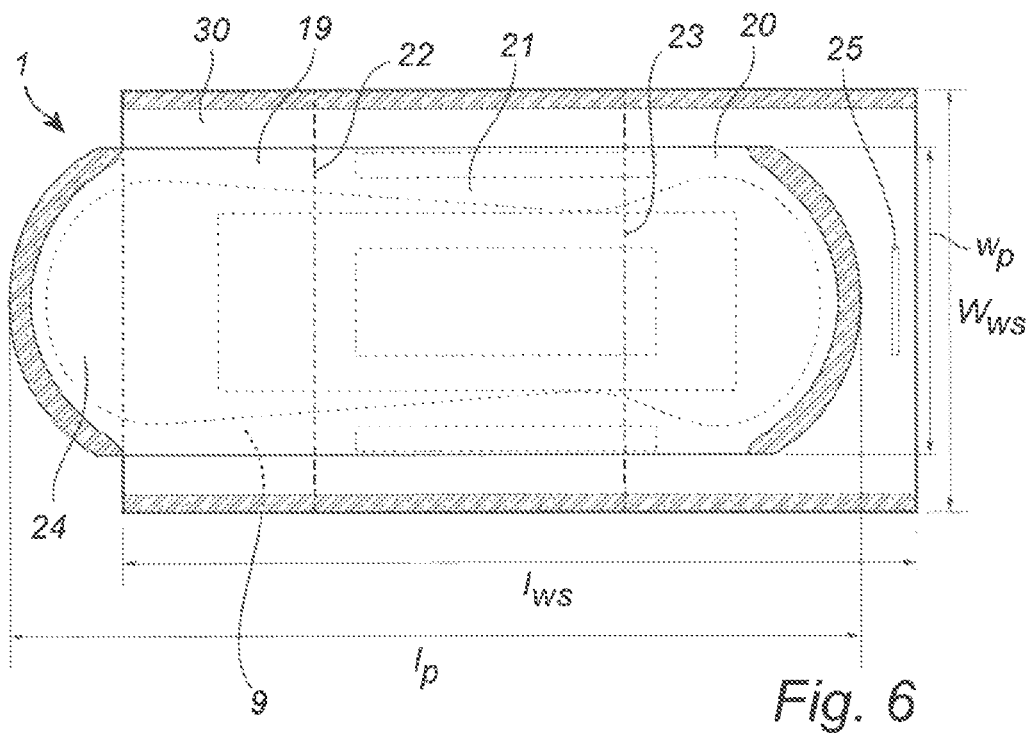
FIG. 6 is a top plan view of a urine incontinence pad and a wrapping sheet.

FIG. 6 illustrates a plan top view of an unfolded incontinence pad 1 with an attached wrapping sheet 30. The urine incontinence pad 1 is a urine incontinence pad according the previous figures. The incontinence pad 1 has a length $l_p$ extending in the longitudinal direction L and a width $w_p$ extending in a transversal direction T. The wrapping sheet 30 has a length $l_{ws}$ extending in the longitudinal direction L and a width $w_{ws}$ extending in the transverse direction T, with the width $w_{ws}$ of the wrapping sheet being greater than the width $w_p$ of the incontinence pad 1. As may be seen in FIG. 6, the wrapping sheet 30 is arranged to cover the backsheet 9 of the incontinence pad 1 of from 75 to 95% of the length $l_p$ of the incontinence pad such that a first end portion 19, corresponding to a rear end portion of the incontinence pad 1 in this figure, has a portion 24 being free from the wrapping sheet 30. The wrapping sheet 30 thus covers the second end portion 20 and the central portion 21 completely, but does not cover the first end portion 19 completely leaving a portion 24 in the rear end of the incontinence pad 1 free from the wrapping sheet 30. The length $l_{ws}$ of the wrapping sheet 30 may thus be equal to or slightly shorter than then the length $l_p$ of the incontinence pad 1.

The incontinence pad 1 is intended to be folded about a first transverse fold line 22 with the first end portion 19 overlying the central portion 21, with a second end portion 20 being folded about a second transverse fold line 23 and overlying the first end portion 19. The wrapping sheet 30 is provided with adhesive 25 in a top edge region for sealing against the wrapping sheet 30 covering the first end portion 19 of the incontinence pad 1 once the incontinence pad 1 and the wrapping sheet 30 has been folded.

The incontinence pad will thus be folded with an incontinence pad rear end portion first and with the front end portion overlaying the rear end portion such that the topsheet in the front end portion is in contact with the backsheet in the portion being free from the wrapping sheet and with the wrapping sheet covering the remaining portion of the incontinence pad rear end portion.

Thickness Measurement

The thickness is determined by means of a measuring foot with affixed load of 0.5 kPa or 2.5 kPa. The foot is lowered onto the sample at a rate of 13 mm/s. The thickness is read off at the digital thickness gauge/tester after 5 seconds when the measuring foot has touched the surface of the sample. If the first absorbent layer in at least a part of said intermediate portion and/or front portion has an opening extending from a body facing side to a garment side, the thickness is determined in the part outside the opening, so that the thickness of the first absorbent layer is included in the thickness T1.

The invention claimed is:

1. A urine incontinence pad having longitudinal side edges extending in a longitudinal direction and transverse end edges, and comprising
   a fluid permeable topsheet, a backsheet and an absorbent core being located between said topsheet and said backsheet,
   said absorbent core having a core front edge, a core rear edge, a core first longitudinal side edge and a core second longitudinal side edge,
   said absorbent core comprising a first core layer and a fluid control layer,
   said absorbent core in the longitudinal direction having a front portion, a rear portion and an intermediate portion located between said front portion and said rear portion, said front portion and said rear portion each having a length of about 30% of the total length of said absorbent core and said intermediate portion having a length of about 40% of the total length of said absorbent core,
   said first core layer extending over said front portion, said intermediate portion and said rear portion, said fluid control layer being shorter than said first core layer and extending in said front portion and said intermediate portion,
   said first core layer comprises 100 gsm superabsorbent material or more,
   said absorbent core having a varying thickness profile as seen in said longitudinal direction, with a first thickness (T1) in said intermediate portion and a second thickness (T2) in said rear portion,
   wherein said first thickness (T1) in said intermediate portion is from 9 mm or more and said second thickness (T2) is from 4 to 0.3 mm, as measured under a load of 0.5 kPa,
   and a region having said second thickness (T2) extends 30 mm or more in the longitudinal direction from said core rear edge and toward said core front edge.

2. The urine incontinence pad according to claim 1, wherein said second thickness (T2) is from 3.5 to 0.3 mm.

3. The urine incontinence pad according to claim 1, wherein said first thickness is from 9 mm to 16 mm.

4. The urine incontinence pad according to claim 1, wherein said absorbent core has a third thickness (T3) in said front region, said third thickness (T3) being 4 mm or less, and said region having said third thickness (T3) extending from said core front edge and toward said core rear edge.

5. The urine incontinence pad according to claim 4, wherein said region having said third thickness (T3) extend 15 mm or more from said core front end edge and toward said core rear edge.

6. The urine incontinence pad according to claim 4, wherein said varying thickness profile as seen in said longitudinal direction of said absorbent core has a fourth thickness (T4) in said rear portion or in a transitional region comprising a part of said intermediate portion and a part of said rear portion, said fourth thickness (T4) being from 4.5 mm to 8.5 mm.

7. The urine incontinence pad according to claim 1, wherein said intermediate portion has a first thickness (T1) under a load of 0.5 kPa and a first compressed thickness under a load of 2.5 kPa, and wherein a difference between said first thickness (T1) and said first compressed thickness under a load is less than 25%.

8. The urine incontinence pad according to claim 1, wherein said absorbent core has said first thickness (T1) in from 5 to 15% of the total longitudinal length of said absorbent core in said front portion, in a portion extending from said intermediate portion and towards said core front edge.

9. The urine incontinence pad according to claim 1, wherein said absorbent core comprises from 200 gsm to 1000 gsm superabsorbent material at least in a part of said absorbent core having said first thickness (T1).

10. The urine incontinence pad according to claim 1, wherein said first layer comprises from 100 to 200 gsm superabsorbent material.

11. The urine incontinence pad according to claim 1, wherein said first core layer has a waist portion located in said front portion or between said front portion and said intermediate portion, a width of said waist portion being 50-75% of a widest transverse width of said front portion of said first absorbent layer.

12. The urine incontinence pad according to claim 1, wherein said first absorbent layer has an opening extending there through from a body-facing side of said first absorbent layer to a garment facing side of said first absorbent layer, said opening extending in said front portion and said intermediate portion.

13. The urine incontinence pad according to claim 1, wherein a widest transverse width of said rear portion is from 80-120 mm.

14. The urine incontinence pad according to claim 1, wherein an elastic member is arranged along each longitudinal side edge of said incontinence pad, at least laterally outside of a transition between said front portion and said intermediate portion of said absorbent core.

15. The urine incontinence pad according to claim 1, wherein said fluid control layer being shorter than said first core layer does not extend into the rear portion of said absorbent core.

16. The urine incontinence pad according to claim 1, wherein said first core layer is arranged between said fluid control layer and said fluid permeable topsheet.

17. The urine incontinence pad according to claim 1, wherein said absorbent core comprises a fluid storage layer arranged between said fluid control layer and said backsheet.

18. The urine incontinence pad according to claim 17, wherein said fluid storage layer is shorter than said first core layer in each of said front portion and said rear portion and longer than said fluid control layer in said front portion and said intermediate portion, as seen in a longitudinal direction.

19. An individually wrapped urine incontinence pad, comprising a urine incontinence pad and a wrapping sheet, urine incontinence pad being a urine incontinence pad according to claim 1, said incontinence pad having a length extending in said longitudinal direction and a width extending in a transverse direction, said wrapping sheet having a length extending in said longitudinal direction and a width extending in said transverse direction, said wrapping sheet being arranged to cover said backsheet of said incontinence pad of from 75 to 95% of said length of said incontinence pad such that a first end portion, corresponding to a rear end portion of said incontinence pad, has a portion being free from said wrapping sheet, said incontinence pad being folded about a first transverse fold line with said first end portion overlying a central portion, with a second end portion being folded about a second transverse fold line and overlying said first end portion.

20. A stack of folded incontinence pads, comprising a plurality of urine incontinence pads according to claim 6, wherein each of said folded incontinence pads of said plurality of folded incontinence pads is folded about a first transverse fold line with a first end portion, overlying a central portion, with a second end portion being folded about a second transverse fold line and overlying said first end portion, wherein said absorbent core has said second thickness (T2) or said fourth thickness (T4) at said first or said second transverse fold line and has said first thickness (T1) at the other one of said first or said second transverse fold line, said stack of folded incontinence pads being stacked in a head-to-toe relationship.

* * * * *